United States Patent
Jörgensen

(10) Patent No.: US 8,265,465 B2
(45) Date of Patent: Sep. 11, 2012

(54) PEBBLE STONE-SHAPED AROMA DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 523 days.

(21) Appl. No.: 12/609,104

(22) Filed: Oct. 30, 2009

(65) Prior Publication Data

US 2011/0103776 A1    May 5, 2011

(51) Int. Cl.
*A01G 13/06* (2006.01)
*B01J 10/00* (2006.01)
(52) U.S. Cl. .................................... 392/386; 422/129
(58) Field of Classification Search .............. 392/386, 392/387–406; 422/129, 162, 166
See application file for complete search history.

(56) References Cited

U.S. PATENT DOCUMENTS

| | | | |
|---|---|---|---|
| 5,189,947 A * | 3/1993 | Yim | 99/415 |
| 7,186,385 B2 * | 3/2007 | Ganguli et al. | 422/129 |
| 7,429,361 B2 * | 9/2008 | Ganguli et al. | 422/129 |
| 7,569,191 B2 * | 8/2009 | Ganguli et al. | 422/129 |
| 7,744,833 B2 * | 6/2010 | Varanasi et al. | 422/306 |
| 7,840,122 B1 * | 11/2010 | Hanrahan et al. | 392/386 |
| 8,107,799 B2 * | 1/2012 | Hirth et al. | 392/397 |

* cited by examiner

*Primary Examiner* — Daniel L Robinson
(74) *Attorney, Agent, or Firm* — Ming Chow; Sinorica, LLC

(57) ABSTRACT

A pebble stone-shaped aroma diffuser includes a top cover shell, an upper panel, a gasket ring, a lower panel, a bottom cover shell, a heater and a base member. The gasket ring is tightly set between the top cover shell and the upper panel, thereby forming with the top cover shell and the upper panel a fluid container. The lower panel is supported on the bottom cover shell and closely attached to the upper panel of the fluid container. The heater is kept in contact with the bottom side of the lower panel. The base member is arranged at the bottom side of the bottom cover shell to provide power supply to the heater for producing heat that is transferred through the lower panel and the upper panel to heat the aromatic fluid in the fluid container. The fluid container is rapidly detachable from the lower panel for cleaning.

10 Claims, 5 Drawing Sheets

PEBBLE STONE-SHAPED AROMA DIFFUSER

BACKGROUND OF THE INVENTION

1. Field of the Invention

The present invention relates to an aromatic diffuser and more particularly, to a pebble stone-shaped diffuser, which assures a high level of safety and facilitates installation and cleaning.

2. Description of the Related Art

Scholars and persons of refined tastes love beautiful natural objects such as natural rocks and pebble stones. Natural rocks and pebble stones may be arranged in the yard or inside the house for decoration to create a visual scene. Further, an aroma diffuser may be placed in displayed rocks or pebble stones to diffuse a beautiful smoke and a pleasant smell, comforting people.

Conventional small-sized aroma diffusers are commonly made of ceramics. However, thick ceramic wall cannot transfer heat energy rapidly, and a thin ceramic wall tends to break. Further, conventional small-sized aroma diffusers commonly have a narrow bottleneck for output of diffused aromatic smoke and use a low or medium temperature heater for heating the contained aromatic fluid or essential oil. It takes much tie to heat the aromatic fluid into vapor for diffusing through the narrow bottleneck into the outside open air.

Further, conventional small-sized aroma diffusers use screws to affix component parts together. When a cleaning work is necessary, it takes much time ad labor to dismount the component parts for cleaning. Further, these conventional small-sized aroma diffusers do not have an attractive outer appearance for use as an indoor decorative item.

Further, conventional small-sized aroma diffusers, more particularly, the bottle-shaped aroma diffusers tend to fall and to break, i.e., conventional small-sized aroma diffusers are not safe in use.

SUMMARY OF THE INVENTION

The present invention has been accomplished under the circumstances in view. It is main object of the present invention to provide a pebble stone-shaped aroma diffuser, which facilitates installation and cleaning, assuring a high level of safety.

To achieve this and other objects of the present invention, a pebble stone-shaped aroma diffuser comprises a top cover shell, an upper panel, a gasket ring, a lower panel, a bottom cover shell, a heater and a base member. The top cover shell comprises a top wall, a bottom edge and an accommodation chamber and an opening located on the top wall. The opening has a caliber smaller than the face width of the accommodation chamber. The upper panel is made from a heat transfer material and fastened to the bottom edge of the top cover shell, having a top wall and a bottom wall. The gasket ring is set in between the top cover shell and the upper panel around the accommodation chamber such that the top cover shell, the upper panel and the gasket ring constitute a fluid container. The lower panel is made from a heat transfer material, having a top wall and a bottom wall. The top wall of the lower panel is attached to the bottom wall of the upper panel. The bottom cover shell has a top edge attached to the bottom wall of the lower panel and an inside pace defined therein. The heater is mounted in the inside space of the bottom cover shell and kept in contact with the top wall of the lower panel and controllable to produce heat to the upper panel. The base member is provided at the bottom side of the bottom cover shell, holding a power cord that is electrically connected to the heater to provide electricity to the heater for producing heat to the lower panel and the upper panel.

When compared to conventional bottle type aroma diffusers that have the drawbacks of cleaning inconvenience and being easy to fall and to break, the assembly of the fluid container and bottom cover shell of the pebble stone-shaped aroma diffuser has a flat shape and strong structural strength and can be positioned on the top of a table steadily. Further, the top cover shell and the upper panel of the fluid container can be made from a metallic or compound ceramic material so that the fluid container does not break easily.

Further, the fluid container can be separated from the lower panel easily, facilitating cleaning.

Further, the op cover shell comprises an inside step defined between the bottom edge and the accommodation chamber thereof and a plurality of bottom mounting holes located on the inside step. Further, the upper panel comprises a plurality of mounting through holes respectively fastened to the bottom mounting holes of the top cover shell with respective fastening members. Further, the gasket ring is squeezed between the inside step of the top cover shell and the top wall of the upper panel around the fastening members.

DETAILED DESCRIPTION OF THE PREFERRED EMBODIMENT

Figure 1:
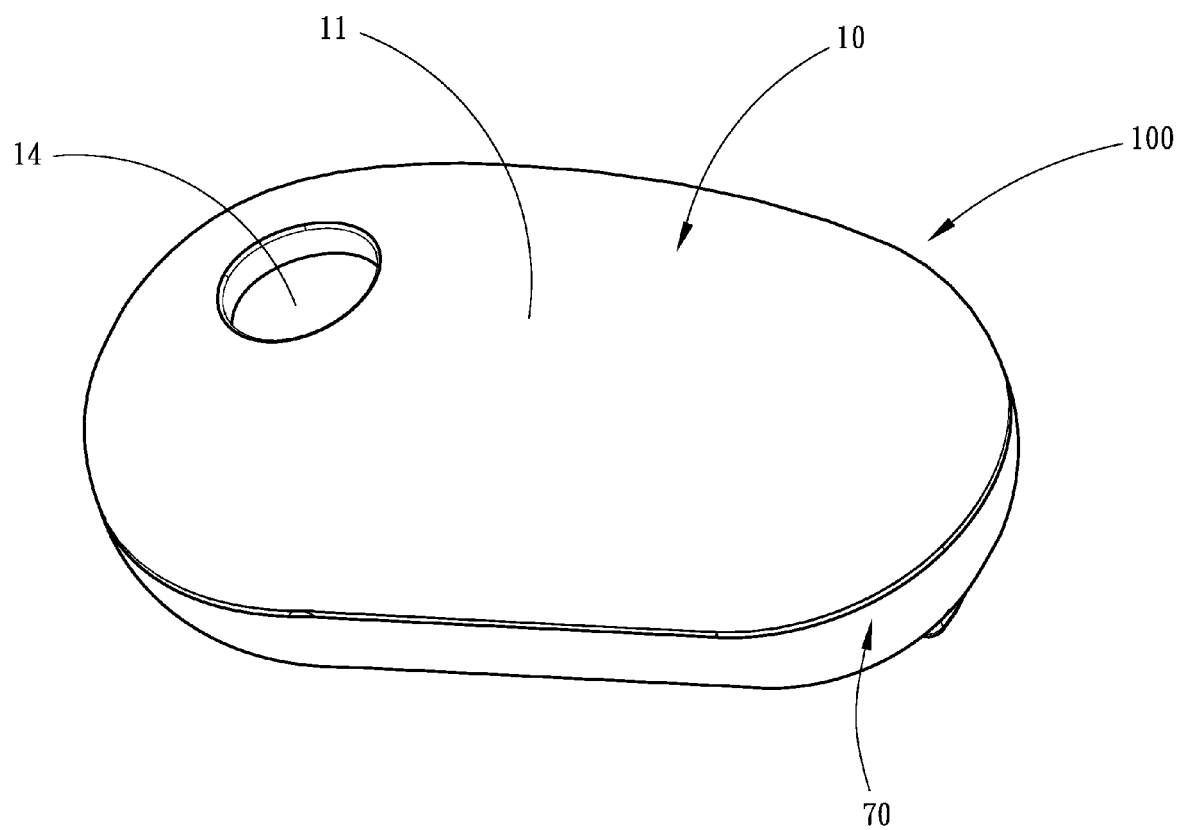
FIG. 1 is an oblique elevation of a pebble stone-shaped aroma diffuser in accordance with the present invention.
Figure 2:
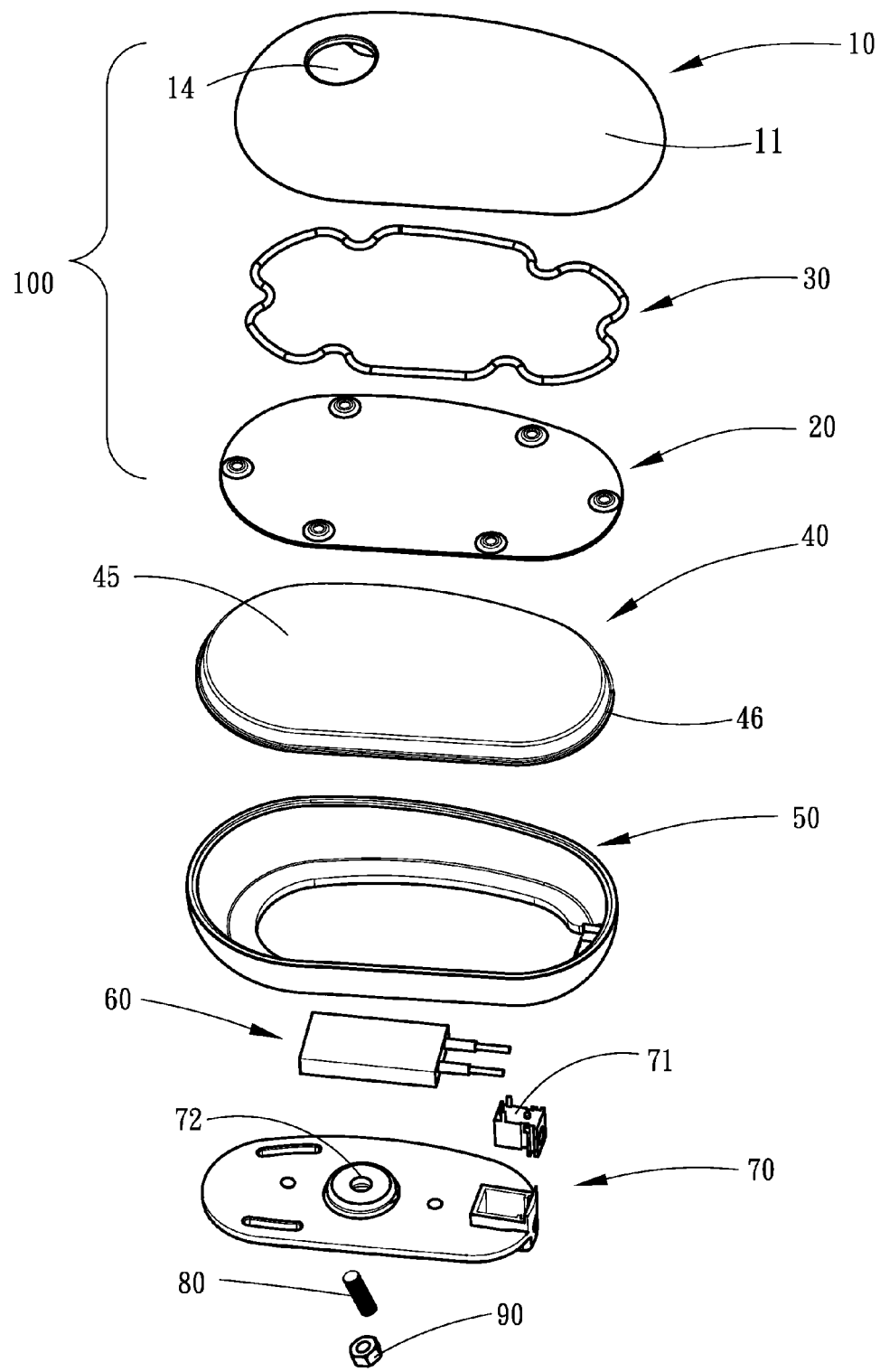
FIG. 2 is a top exploded view of the pebble stone-shaped aroma diffuser in accordance with the present invention.

Referring to FIGS. 1 and 2, a pebble stone-shaped aroma diffuser in accordance with the present invention is shown comprising a top cover shell 10, an upper panel 20, a gasket ring 30, a lower panel 40, a bottom cover shell 50, a heater 60 and a base member 70. The top cover shell 10, the upper panel 20 and the gasket ring 30 constitute a fluid container 100 for holding an aromatic fluid.

Figure 3:
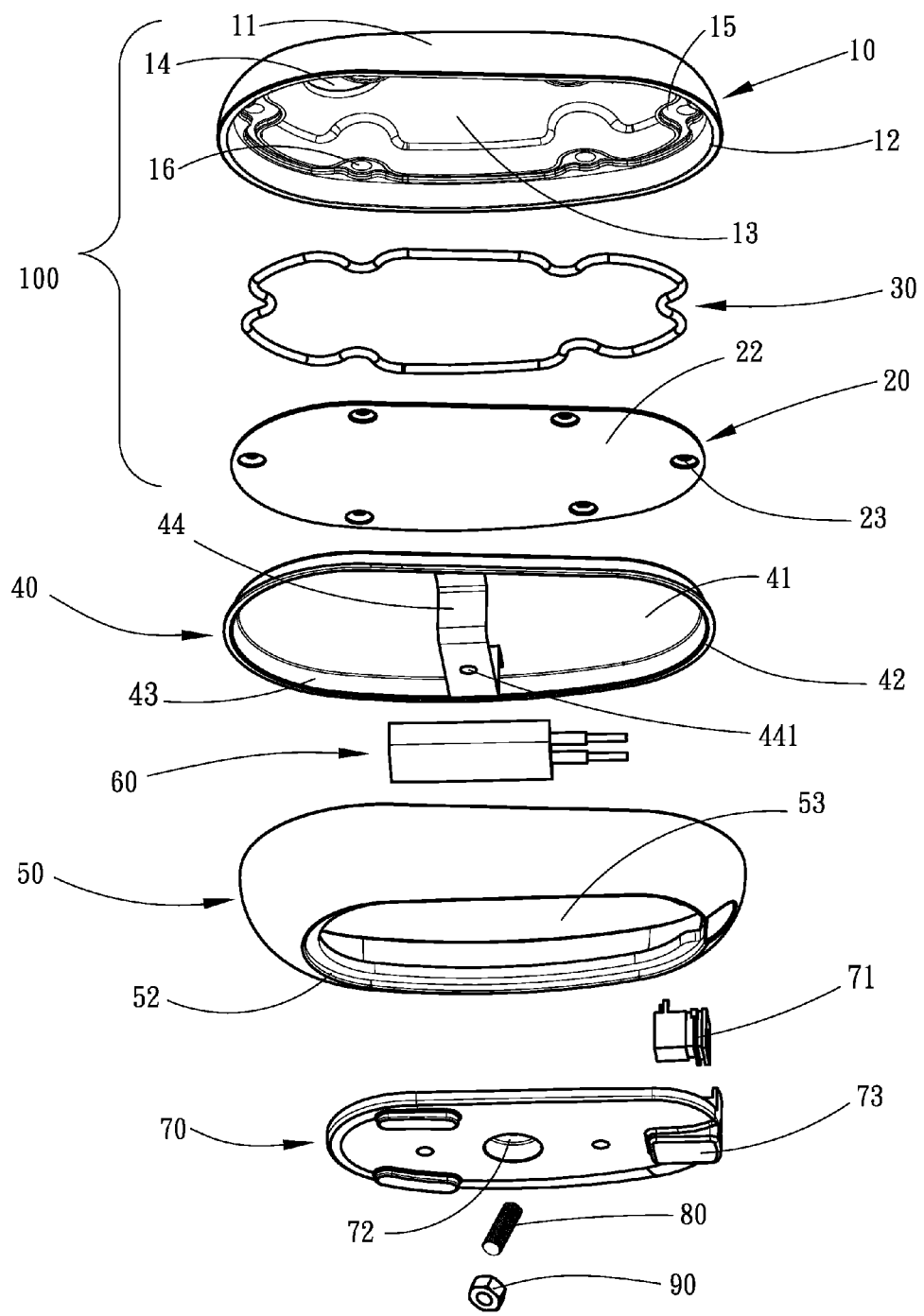
FIG. 3 is a bottom exploded view of the pebble stone-shaped aroma diffuser in accordance with the present invention.
Figure 4:
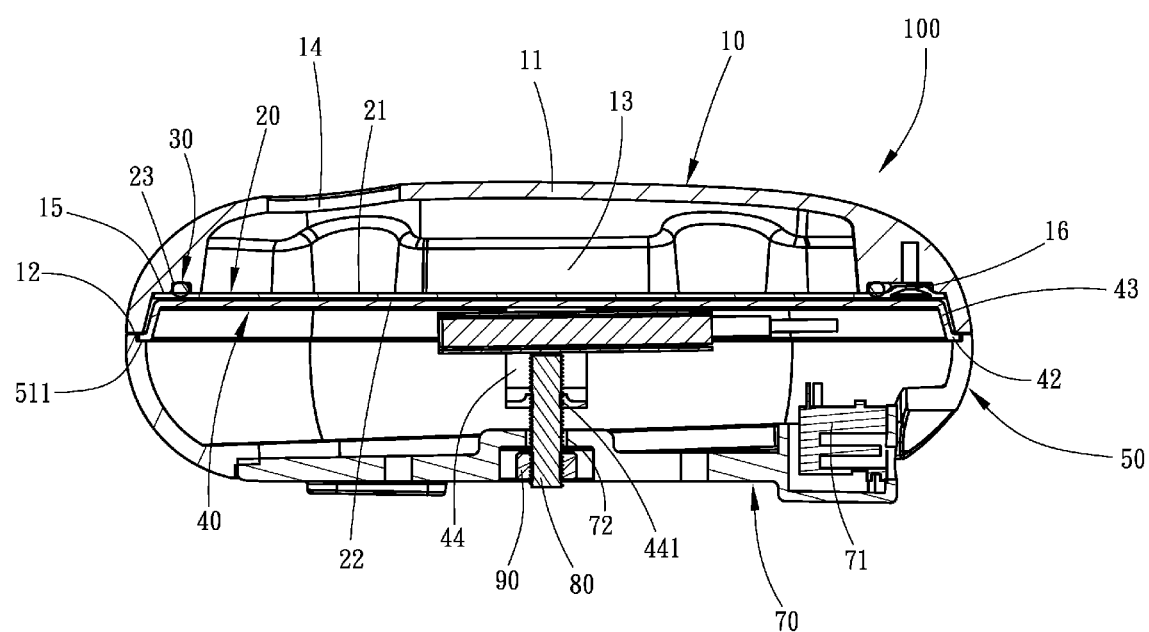
FIG. 4 is a sectional assembly view of the pebble stone-shaped aroma diffuser in accordance with the present invention.

Referring to FIGS. 3 and 4, the top cover shell 10 is preferably made from melamine for the advantages of light weight, high durability and non-fragility. The top cover shell 10 has a top wall 11, a bottom edge 12, an accommodation chamber 13, an opening 14 located on the top wall 11, an inside step 15 and a plurality of bottom mounting holes 16. The diameter of the opening 14 is much smaller than the face width of the accommodation chamber 13. The inside step 15 is defined between the bottom edge 12 and the accommodation chamber 13. The bottom mounting holes 16 are located on the inside step 15 and upwardly extended therefrom. The bottom edge 12 protrudes downwards over the bottom mounting holes 16 to a predetermined distance.

The upper panel 20 is made from metal. Further, the upper panel 20 is fastened to the bottom edge 12 of the top cover shell 10, having a top wall 21, a bottom wall 22 and a plurality of mounting through holes 23. The top wall 21 of the upper panel 20 is connected to the inside step 15 of the top cover shell 10.

The gasket ring 30 is sealed in between the top cover shell 10 and the upper panel 20 around the accommodation chamber 13 and closely attached to the fastening members (not shown) that are mounted in the mounting through holes 23 of the upper panel 20 and the bottom mounting holes 16 of the top cover shell 10 to affix the top cover shell 10 and the upper panel 20 together. Thus, the top cover shell 10, the upper panel 20 and the gasket ring 30 constitute a fluid container 100 for holding an aromatic fluid. After installation, the gasket ring 30 is tightly squeezed between the inside step 15 of the top cover shell 10 and the top wall 21 of the upper panel 20, obtaining an excellent watertight effect.

The lower panel 40 is a hollow metal panel configured subject to the configuration of the inside step 16 of the top cover shell 10, having a substantially ⊓-shaped cross section. The lower panel 40 has a top wall 41, a bottom edge 42, a peripheral wall 43 connected between the top wall 41 and the bottom edge 42 and a suspension bracket 44. The top wall 41 has a convex top surface 45 fitting the upper board 20. The surface area of the convex top surface 45 is slightly smaller than the area of the lower panel 40 so that a retaining groove 46 is defined around the convex top surface 45 for securing the bottom edge 12 of the top cover shell 10 of the fluid container 100. The convex top surface 45 of the top wall 41 of the lower panel 40 is tightly attached to the bottom wall 22 of the upper panel 20. The suspension bracket 44 is a substantially U-shaped bracket, having a screw hole 441 on the middle.

The bottom cover shell 50 is preferably molded from melamine. The bottom cover shell 50 has a top wall 51, a bottom wall 52 and an inside space 53. The bottom edge 42 of the lower panel 40 is rested on an inner step 511 at the top wall 51 of the bottom cover shell 50. The aforesaid fluid container 100 is detachably stacked on the convex top surface 45 of the top wall 41 of the lower panel 40 to force the bottom edge 12 of the top cover shell 10 into engagement with the retaining groove 46 of the lower panel 40. This detachably arrangement facilitates installation and cleaning.

The heater 60 according to the present preferred embodiment is a cement resistor mounted in the suspension bracket 44 of the lower panel 40 and received inside the inside space 53 of the bottom cover shell 50.

The base member 70 is attached to the bottom wall 52 of the bottom cover shell 50. Further, the base member 70 holds a power cord 71 and has a mounting through hole 72.

Further, a screw rod 80 is threaded through the mounting through hole 72 of the base member 70 into the screw hole 441 of the suspension bracket 44 to stop the heater 60 against the top wall 41 of the lower panel 40, and then a lock nut 90 is threaded onto the screw rod 80 and stopped at the bottom side of the base member 70, thereby affixing the base member 70 to the bottom cover shell 50.

After connection of the power cord 71 to power source, the heater 60 is electrically connected to emit heat to the lower panel 40 and the upper panel 20, thereby heating the aromatic fluid in the fluid container 100.

According to the present preferred embodiment, the upper panel 20, the convex top surface 45 of the top wall 41 of the lower panel 40 and the heater 60 are kept in horizontal and closely attached to one another in a stacked relationship for quick transfer of heat energy evenly.

The base member 70 further has a plurality of foot members 73 disposed at the bottom side for supporting the pebble stone-shaped aroma diffuser stably on a flat surface.

Figure 5:
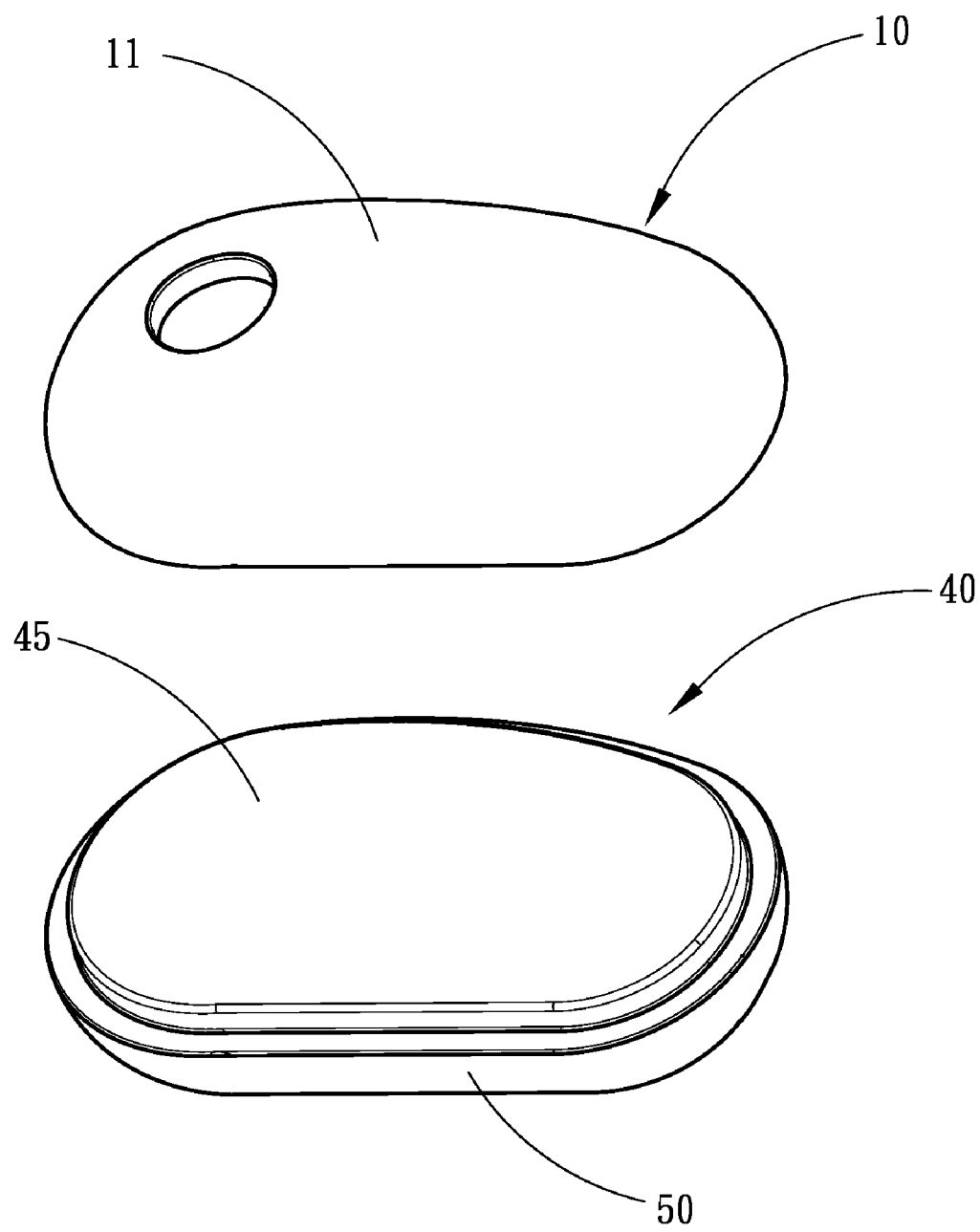
FIG. 5 illustrates the lower panel separated from the bottom cover shell according to the present invention.

When compared to conventional bottle type aroma diffusers that have the drawbacks of cleaning inconvenience and being easy to fall and to break, the assembly of the fluid container 100 and bottom cover shell 50 of the pebble stone-shaped aroma diffuser of the present invention, as shown in FIG. 5, has a flat shape and strong structural strength and can be positioned on the top of a table steadily. Further, the caliber of the opening 14 of the fluid container 100 is much smaller than the face width of the accommodation chamber 13, therefore the internal aromatic fluid will not fall out of the fluid container 100. Further, because the main body of the fluid container 100 is made from melamine in a flat shape, it will not break easily, assuring a high level of safety. Further, the fluid container 100 can easily be disengaged from the retaining groove 46 of the lower panel 40 and separated from the base member 70 and the power cord 71, facilitating safety delivery and cleaning.

After cleaning of the fluid container 100 to remove residual aromatic fluid (essential oil), the bottom edge 12 of the top cover shell 10 of the fluid container 100 can easily be engaged into the retaining groove 46 of the lower panel 40, finishing the installation. Therefore, cleaning of the fluid container 100 is quite simple.

Further, the upper panel 20, the lower panel 40 and the heater 60 are stacked up and kept in horizontal. When the heater 30 starts to emit heat, the broad horizontal structure facilitates quick transfer of heat energy. Further, the upper panel 20 and the lower panel 40 are made from a metal material having high coefficient of heat transfer, facilitating quick and even transfer of heat energy to heat the aromatic fluid.

Further, the heater 60 is an insulative cement resistor meeting USA safety codes. During operation of the heater 60, the temperature of the emitted heat energy is not too high, assuring a high level of safety.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A pebble stone-shaped aroma diffuser, comprising:
   a top cover shell, said top cover shell comprising a top wall, a bottom edge, an accommodation chamber and an opening located on the top wall, said opening having a caliber smaller than the face width of said accommodation chamber;
   an upper panel made from a heat transfer material and fastened to the bottom edge of said top cover shell, said upper panel having a top wall and a bottom wall;
   a gasket ring set in between said top cover shell and said upper panel around said accommodation chamber such that said top cover shell, said upper panel and said gasket ring constitute a fluid container;
   a lower panel made from a heat transfer material, said lower panel having a top wall and a bottom wall, the top wall of said lower panel being attached to the bottom wall of said upper panel;
   a bottom cover shell, said bottom cover shell having a top edge attached to the bottom wall of said lower panel and an inside pace defined therein;
   a heater mounted in the inside space of said bottom cover shell and kept in contact with the top wall of said lower panel and controllable to produce heat to said upper panel; and
   a base member provided at a bottom side of said bottom cover shell, said base member holding a power cord electrically connected to said heater for providing electricity to said heater to heat said lower panel and said upper panel.

2. The pebble stone-shaped aroma diffuser as claimed in claim 1, wherein said top cover shell and said bottom cover shell are made from melamine.

3. The pebble stone-shaped aroma diffuser as claimed in claim 1, wherein said upper panel and said lower panel are made from metal.

4. The pebble stone-shaped aroma diffuser as claimed in claim 1, wherein said top cover shell and said bottom cover shell are made from metal.

5. The pebble stone-shaped aroma diffuser as claimed in claim 1, further comprising a suspension bracket mounted in the bottom wall of said upper panel to support said heater, and fastening means extending upwards from said base member and fastened to said suspension bracket to lock said heater to the bottom wall of said lower panel.

6. The pebble stone-shaped aroma diffuser as claimed in claim 5, wherein said suspension bracket has a screw hole; said fastening means comprises a screw rod threaded into said screw hole of said suspension bracket and stopped against said heater to force said heater upwards against the bottom wall of said upper panel.

7. The pebble stone-shaped aroma diffuser as claimed in claim 5, wherein said base member comprises a mounting through hole; said screw member is inserted through said mounting through hole and threaded into said screw hole; said fastening means further comprising a lock nut threaded onto one end of said screw and stopped at a bottom side of said base member.

8. The pebble stone-shaped aroma diffuser as claimed in claim 1, wherein said top cover shell comprises an inside step defined between the bottom edge and the accommodation chamber thereof and a plurality of bottom mounting holes located on said inside step; said upper panel comprises a plurality of mounting through holes respectively fastened to the bottom mounting holes of said top cover shell with respective fastening members; said gasket ring is squeezed between said inside step of said top cover shell and the top wall of said upper panel around said fastening members.

9. The pebble stone-shaped aroma diffuser as claimed in claim 1, wherein said heater is a cement resistor.

10. The pebble stone-shaped aroma diffuser as claimed in claim 1, wherein said base member comprises a plurality of foot members equiangularly spaced on a bottom side thereof.

* * * * *